United States Patent [19]

Sanderson et al.

[11] Patent Number: 5,159,122

[45] Date of Patent: Oct. 27, 1992

[54] CATALYTIC DECOMPOSITION OF PEROXIDE IMPURITIES IN A METHYL TERTIARY BUTYL ETHER RECYCLE STREAM

[75] Inventors: John R. Sanderson, Leander; John F. Knifton; Neal J. Grice, both of Austin, all of Tex.

[73] Assignee: Texaco Chemical Company, White Plains, N.Y.

[21] Appl. No.: 833,224

[22] Filed: Feb. 10, 1992

[51] Int. Cl.$^5$ ............................................. C07C 41/36
[52] U.S. Cl. .................................................. 568/699
[58] Field of Search .......................................... 568/699

[56] References Cited

U.S. PATENT DOCUMENTS 5,099,072  3/1992  Knifton ............................... 568/698

*Primary Examiner*—Howard T. Mars
*Attorney, Agent, or Firm*—Jack H. Park; Kenneth R. Priem; Carl G. Ries

[57] ABSTRACT

Peroxides such as di-tert-butyl peroxide, present in a methyl-tert-butyl ether recycle stream, may be removed by bringing the recycle stream into contact with an acid treated clay. The peroxides are decomposed to tert-butyl alcohol (main product) plus minor amounts of acetone and methanol. Since the recycle stream consists mainly of tert-butyl alcohol and methanol, methyl-tert-butyl ether is also formed in significant quantities. Isobutylene is also formed by dehydration of the tert-butyl alcohol.

6 Claims, 1 Drawing Sheet

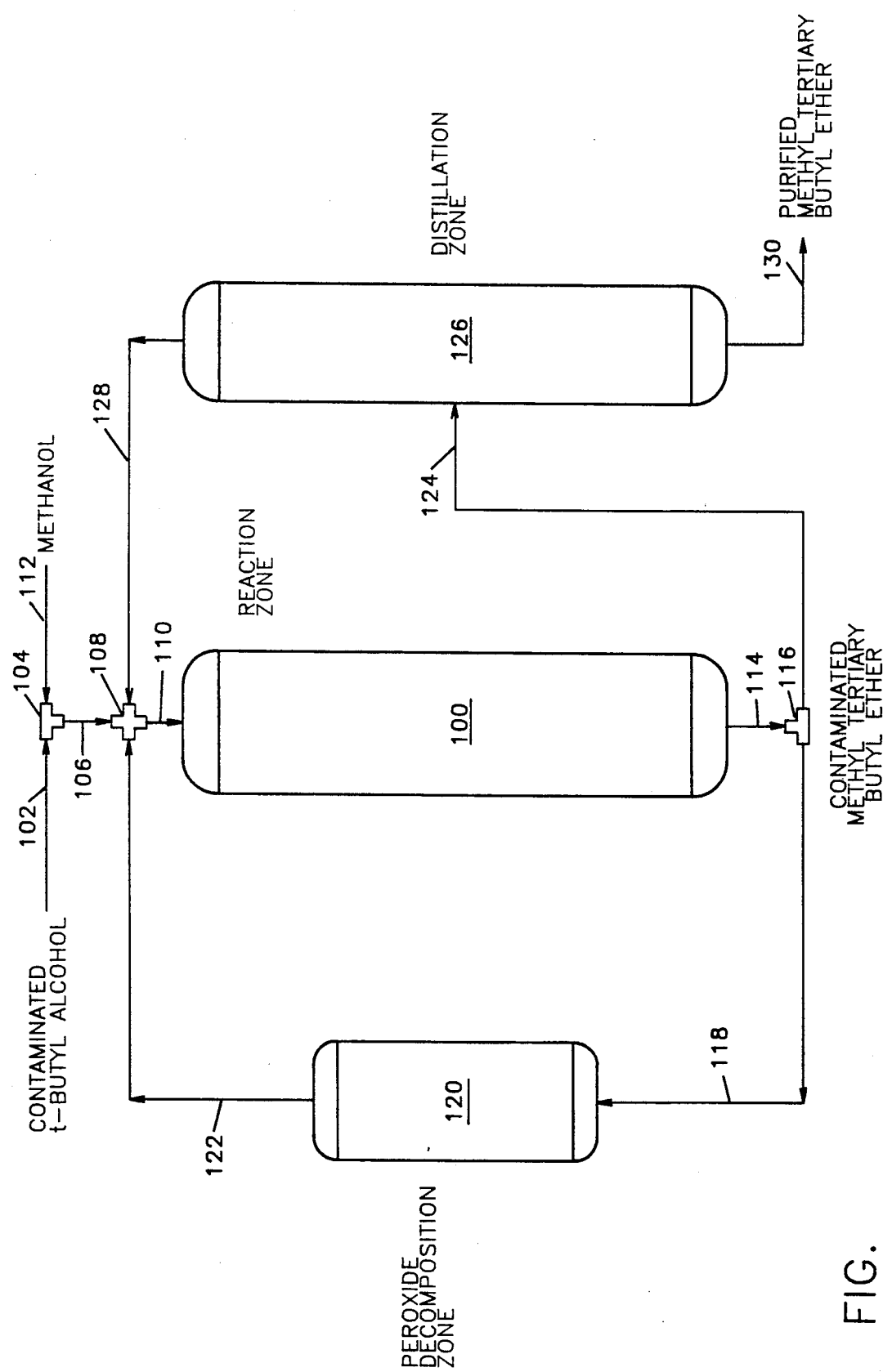
FIG.

CATALYTIC DECOMPOSITION OF PEROXIDE IMPURITIES IN A METHYL TERTIARY BUTYL ETHER RECYCLE STREAM

BACKGROUND OF THE INVENTION

1. Field of the Invention

This invention relates to the catalytic purification of a methyl tertiary butyl ether (MTBE) recycle stream contaminated with trace quantities of ditertiary butyl peroxide and other peroxides. More particularly, this invention relates to a method for the removal of residual contaminating quantities of peroxides such as ditertiary butyl peroxide (DTBP) from a methyl tertiary butyl ether recycle stream which is prepared by the reaction of methanol with tertiary butyl alcohol (TBA) and is useful as an octane-enhancing component for motor fuels. In accordance with the present invention the peroxide-contaminated recycle stream is brought into contact with an acid treated clay catalyst in order to substantially selectively decompose peroxides such as ditertiary butyl peroxide.

Peroxides such as di-tert-butyl peroxide, present in a methyl-tert-butyl ether recycle stream, may be removed by bringing the recycle stream into contact with an acid treated clay. The peroxides are decomposed to tert-butyl alcohol (main product) plus minor amounts of acetone and methanol. Since the recycle stream consists mainly of tert-butyl alcohol and methanol, methyl-tert-butyl ether is also formed in significant quantities. Isobutylene is also formed by dehydration of the tert-butyl alcohol.

2. Prior Art

It is known to those skilled in the art that ethers, including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently commercial processes for the manufacture of methyl tert-butyl ether are based upon the liquid-phase reaction of isobutylene and methanol (Eq. 1), catalyzed by a cationic ion-exchange resin (see, for example: Hydrocarbon Processing, Oct. 1984, p. 63; Oil and Gas J., Jan. 1, 1979, p. 76; Chem. Economics Handbook-SRI, Sept. 1986, p. 543-7051P). The cationic ion-exchange resins used in MTBE synthesis normally have the sulphonic acid functionality (see: J. Tejero, J. Mol. Catal., 42 (1987) 257; C. Subramamam et al., Can. J. Chem. Eng., 65 (1987) 613).

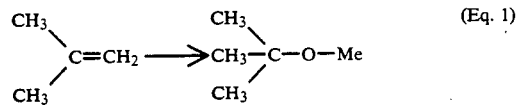

(Eq. 1)

With the expanding use of MTBE as an acceptable gasoline additive, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block. It would be advantageous to have an efficient process for making MTBE by reaction of methanol with tertiary butyl alcohol, since t-butanol (TBA) is readily available commercially through isobutane oxidation. However, as hereafter more fully explained, when tertiary butyl alcohol is prepared by first oxidizing isobutane to form tertiary butyl hydroperoxide and by then thermally or catalytically converting the tertiary butyl hydroperoxide to tertiary butyl alcohol, a number of oxygenation by-products are formed, including ditertiary butyl peroxide and other alkyl peroxides. The oxygenation by-products adversely affect the quality of the tertiary butyl alcohol and methyl tertiary butyl ether made therefrom and are removed only with difficulty.

There is a substantial body of prior art directed to the purification of methyl tertiary butyl ether prepared from isobutylene and methanol. In this situation, the oxygenation by-products are not present in either of the feed materials or in the methyl tertiary butyl ether product.

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether raffinate plus ether-methanol bottoms, the latter being azeotropically distilled to yield ether-methanol overhead which is recycled to water washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any major problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

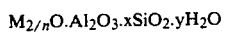

where M is an alkali metal or alkaline earth metal cation or organic base cation, n is the valence of the cation and x and y are variables.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In U.S. Pat. No. 4,822,921 there is disclosed a method for producing MTBE by reacting tertiary butyl alcohol and methanol in the presence of a catalyst comprising an inert support, such as titania, having a phosphoric acid impregnated thereon.

U.S. Pat. No. 4,827,048 discloses a method for producing MTBE by reacting tertiary butyl alcohol and methanol in the presence of a catalyst comprising a heteropoly acid such as 12-tungstophosphoric acid or 12-molybdophosphoric acid on an inert support, such as titania.

In copending U.S. patent application Ser. No. 07/494,281, there is disclosed a method for preparing methyl tertiary butyl ether by reacting butanol and methanol in the presence of a catalyst comprising a super-acid alumina or a faujasite-type zeolite.

Sanderson U.S. Pat. No. 4,900,850 discloses a method for removing ditertiary butyl peroxide from t-butyl alcohol by water extraction.

Sanderson et al. also disclose catalytic methods for the purification of t-butyl alcohol contaminated with residual quantities of tertiary butyl hydroperoxide and ditertiary butyl peroxide using catalysts composed of mixtures of nickel, copper, chromia and iron (U.S. Pat. No. 4,704,482), catalysts composed of mixtures of iron, copper, chromia and cobalt (U.S. Pat. No. 4,705,903), catalysts composed of mixtures of nickel, copper, chromium and barium (U.S. Pat. No. 4,873,380), or catalysts composed of metals selected from group VIB or VIIIB of the Periodic Table (U.S. Pat. No. 4,742,179).

It has heretofore been proposed, as shown, for example, by Grane U.S. Pat. No. 3,474,151 to thermally decompose tertiary butyl hydroperoxide and ditertiary butyl peroxide to form tertiary butyl alcohol. The thermal decomposition must be conducted with care, as pointed out by Grane, in that tertiary butyl alcohol will start to dehydrate at a temperature of about 450° F. and in that the dehydration becomes rapid at temperatures above about 475° F. Moreover, the product from the thermal decomposition normally contains a minor amount of tertiary butyl hydroperoxide and ditertiary butyl peroxide which have an adverse effect upon the quality of motor fuels and must be substantially completely removed if the tertiary butyl alcohol is to be fully effective. Grane proposes to accomplish this thermally by heating tertiary butyl alcohol containing small quantities of such peroxides at a temperature of 375°-475° F. for a period of 1 to 10 minutes.

This concept was expanded upon by Grane et al. in U. S. Pat. Nos. 4,294,999 and 4,296,262 to provide integrated processes wherein, starting with isobutane, motor-fuel grade tertiary butyl alcohol was prepared by the oxidation of isobutane (e.g., in the presence of a solubilized molybdenum catalyst) to produce a mixture of tertiary butyl alcohol and tertiary butyl hydroperoxide from which a fraction rich in tertiary butyl hydroperoxide could be recovered by distillation. This stream, after being debutanized was subjected to thermal decomposition under pressure at a temperature of less than 300° F. for several hours to significantly reduce the concentration of the tertiary butyl hydroperoxide. However, the product of this thermal decomposition step still contained residual tertiary butyl hydroperoxide, most of which was thereafter removed by a final thermal treatment of the contaminated tertiary butyl hydroperoxide in the manner taught by Grane U.S. Pat. No. 3,474,151.

Thus, the removal of trace quantities of tertiary butyl hydroperoxide from motor grade tertiary butyl alcohol has received appreciable attention. However, little appears to have been published concerning the removal of trace quantities of ditertiary butyl peroxide, the more refractory of the two peroxides. This may be explainable both because ditertiary butyl peroxide is not always present in trace quantities in motor grade tertiary butyl alcohol (its presence or absence being a function of the reaction conditions used in oxidizing the isobutane starting material) and because, when present, it is present in significantly lower concentrations. For example, after decomposition of the major amount of tertiary butyl hydroperoxide formed by the oxidation of isobutane, the tertiary butyl hydroperoxide residual content will normally be about 0.1 to about 1 wt.%, based on the tertiary butyl alcohol, while the residual ditertiary butyl peroxide content, if any, will only be about 0.1 to 0.5 wt.%.

It has also been proposed to remove the residual hydroperoxide contaminants from tertiary butyl alcohol through the use of a heterogeneous cobalt oxide catalyst containing a copper oxide promoter as shown, for example, by Coile U.S. Pat. No. 4,059,598. Allison et al. in U.S. Pat. No. 3,505,360 have more generically taught that alkenyl hydroperoxides can be decomposed catalytically through the use of a catalyst based on a metal or compound of a metal of group IV-A, V-A or VI-A.

In West German DE 3248465-A a two-step process is disclosed wherein isobutane is oxidized noncatalytically with air to a conversion of about 48-90% to form the corresponding hydroperoxide, which is then catalytically decomposed under hydrogenation conditions in the presence of a supported catalyst such as palladium, platinum, copper, rhenium, ruthenium or nickel to form tertiary butyl alcohol. The decomposition product obtained using 1.3% palladium on lithium spinel as a catalyst contained significant quantities of acetone, water and methanol.

BACKGROUND

When isobutane is reacted with molecular oxygen the principal products of the reaction are tertiary butyl alcohol and tertiary butyl hydroperoxide. However, minor amounts of other peroxides, including ditertiary butyl peroxide, are also formed. Generally speaking, from about 10 to about 100 parts of tertiary butyl hydroperoxide are formed per part of ditertiary butyl peroxide. Minor quantities of other contaminants are also formed.

A listing of the components present in a representative reaction product, and their nominal boiling points is given in Table A.

TABLE A

| Component | NBP (°C.) |
|---|---|
| Isobutane | −11.7 |
| Methyl formate | 31.8 |
| Acetone | 56.3 |
| Isobutylene oxide | 60.0 |

TABLE A-continued

| Component | NBP (°C.) |
|---|---|
| Isobutyraldehyde | 64.1 |
| Methanol | 64.7 |
| Methyl-t-butyl peroxide | 74.2 |
| Isopropyl alcohol | 82.3 |
| Tertiary butyl alcohol | 82.4 |
| Ditertiary butyl peroxide | 111.0 |
| t-butyl-i-pr-peroxide | 124.0 |
| Tertiary butyl formate | 163.8 |

The minor by-products are sometimes difficult to remove. For example, tertiary butyl formate has a higher boiling point than ditertiary butyl hydroperoxide but tends to distill overhead, which suggests that it forms a minimum boiling azeotrope with another component or components.

When tertiary butyl alcohol is prepared by the catalytic decomposition of tertiary butyl hydroperoxide or by the catalytic reaction of tertiary butyl hydroperoxide with an olefin such as propylene, the tertiary butyl alcohol will be contaminated with residual quantities of tertiary butyl hydroperoxide and ditertiary butyl peroxide, as explained above, and if contaminated tertiary butyl alcohol prepared in this manner is used as a feedstock for the direct preparation of MTBE by reaction with methanol, the tertiary butyl hydroperoxide and ditertiary butyl peroxide impurites will remain with the MTBE, and must be removed to the lowest level that is feasibly possible if the MTBE is to be used in the preparation of fuel for internal combustion engines.

SUMMARY OF THE INVENTION

It has been surprisingly discovered in accordance with the present invention that motor-fuel grade methyl tertiary butyl ether (MTBE) that is contaminated with residual amounts of peroxides such as ditertiary butyl peroxide can be effectively treated for the substantially complete removal of such peroxide contaminants by bringing the contaminated MTBE into contact with an acid treated clay catalyst at a superatmospheric pressure at a temperature of about 120° to about 220° C.

It has been further discovered that most of the decomposition products that are formed are decomposition products that can be removed from the MTBE with comparative ease if the treatment with the acid treated clay catalyst is conducted prior to distillation. The principle decomposition products are tertiary butyl alcohol (which does not adversely affect the octane rating of the MTBE product), and methanol and acetone, both of which can be removed from MTBE by distillation.

Quite unexpected and surprising is our discovery that one of the more significant reaction products that is formed by the treatment of a peroxide-contaminated methyl tertiary butyl ether reaction product is methyl tertiary butyl ether. Thus, both the quality and quantity of the methyl tertiary butyl ether reaction product are enhanced through the provision of the process of the present invention.

Isobutylene is also formed in significant quantities, but is not detrimental here since isobutylene can be recycled and reacted with methanol to form MTBE.

Thus, the provision of the process of the present invention wherein a motor fuel grade MTBE feedstock containing contaminating quantities of peroxides such as ditertiary butyl peroxide, is catalytically treated for the decomposition of the peroxides so that they are substantially completely removed and at least partially converted to methyl tertiary butyl ether. This is accomplished without significantly increasing the contamination levels of undesirable contaminants. The net effect, therefore, is an improvement in the quality of the treated methyl tertiary butyl ether by the substantially complete removal of peroxide contaminants and an improvement in the quantity of methyl tertiary butyl ether that is produced. In addition, the treated methyl tertiary butyl ether contains an additional quantity of methyl tertiary butyl ether formed during the decomposition of the peroxide contaminants.

STARTING MATERIALS

The starting materials for the process of the present invention include a motor-fuel grade MTBE feedstock obtained in the manner described above that is contaminated with peroxides such as ditertiary butyl peroxide.

The motor-fuel grade MTBE feedstock will contain contaminating quantities of peroxides such as ditertiary butyl peroxide. The levels of contamination of such materials are such that the tertiary butyl alcohol will normally contain, prior to treatment, from about 0.1 to about 5 wt.% of ditertiary butyl peroxide and other peroxides. Minor quantities of other contaminants may also be present.

Catalytic Treatment of Methyl Tertiary Butyl Ether

In accordance with the present invention, an MTBE feedstock, as above described, is brought into contact with an acid treated clay catalyst of the present invention under reaction conditions correlated to catalytically convert peroxides such as ditertiary butyl peroxide contaminants in the tertiary butyl alcohol feedstock to by-products including tertiary butyl alcohol and acetone with not more than a minor increase in the level of contamination of other by-products.

The reaction may be conducted batchwise in an autoclave using powdered catalyst or may be conducted on a continuous basis by passing the tertiary butyl alcohol through a reactor containing a bed of a catalyst of the present invention under reaction conditions including a temperature within the range of about 100° to about 220° C. and, more preferably, from about 120° to about 180° C. The reaction is suitably conducted at 0 to 10,000 psig., and more preferably at about 200 to about 1,000 psig. When the reaction is conducted batchwise, contact time may suitably be from about 0.5 to about 4 hours. When the reaction is conducted on a continuous basis, the MTBE should be passed over the bed of catalyst at a liquid hourly space velocity of about 0.25 to about 5 pounds of MTBE per hour per pound of catalyst.

The reaction product is suitable for use as feed to an MTBE reactor.

The Acid-Treated Clay Catalyst

The catalyst to be used in accordance with the present invention is an acid-treated clay catalyst. Acid-treated clay catalysts are known articles of commerce.

Chemically, clays are composed primarily of silicon, aluminum and oxygen, with minor amounts of magnesium and iron in some cases. Variations in the ratios of these constituents result in some fifty separate clays, each with its own characteristic properties.

Among the effective clays that may be used in accordance with the present invention are smectite clays. Smectite clays are discussed in an article cited in Chem Systems Report 84-3, 239-249, at Section 3.4320. These clays have a small particle size and unusual intercalation properties which afford them a high surface area. They are aluminosilicates with a unique structure that permits modifications which provide useful catalysts. They comprise layered sheets of octahedral sites between sheets of tetrahedral sites, and the distance between the layers can be adjusted by swelling through treatment with an appropriate solvent, or treatment with a pillaring or Lewis acid reagent, etc. What renders the smectites of particular interest among the clay minerals is their cation exchange, intercalation and swelling properties.

The three-layered sheet types of smectite clays include montmorillonite, vermiculite and certain micas, all of which may be expanded between their layers by an appropriate treatment. The idealized basic structure of clays of this type is that of pyrophylite which has the basic formula $SiAl_4O_{20}(OH)_4$.

For example, montmorillonite clays may be represented by the formula:

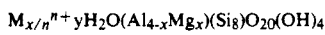

$$M_{x/n}{}^{n+} yH_2O(Al_{4-x}Mg_x)(Si_8)O_{20}(OH)_4$$

where M represents the interlamellar (balancing cation, normally sodium or lithium) and x, y and n are integers.

Commercial clays, such as montmorillonite clays, are normally treated with an acid, such as a mineral acid, in order to improve their utility. Acids, particularly mineral acids such as sulfuric acid, phosphoric acids or hydrochloric acid "activate" mon-morillonite clays by attacking and solubilizing structural cations in the octahedral crystalline structure of the clay. This opens up the clay structure and increases surface area. These acid-treated clays, particularly those treated with mineral acids, act as stong Bronsted acids.

Acid-treated montmorillonite clays constitute a preferred type of smectite clays for us in accordance with the present invention. Preferably these acid clays should have acidities in the range of 3 to 20 or greater, mg. KOH/gm, titrated to a phenolphthalein end point. Their surface area should be greater than 30 m$^2$/g and preferably 200 to 1,000 m$^2$/g. Their moisture content is preferably limited such that upon heating to 220° F. the weight loss is less than 20 wt.%.

Illustrative examples of suitable montmorillonite clays include powdered clays, such as Engelhard's Filtrol Grade 13, 113 and 160, clays in granular form, such as Engelhard Filtrol Grade 24, having a 20-60 mesh (herein sometimes referred to as "Clay 24"), as well as extruded clays such as Engelhard Filtrol Clay 62, sold as 1/16" and 3/16" diameter extrudates, all sold by Engelhard.

Catalytic Treatment of Methyl Tertiary Butyl Ether

In accordance with the present invention, a methyl tertiary butyl ether feedstock contaminated with oxygenated impurities including ditertiary butyl peroxide and lesser amounts of other peroxides is brought into contact with a catalyst of the present invention under reaction conditions correlated so as to substantially selectively convert the peroxide contaminants to conversion side products including methyl tertiary butyl ether, tertiary butyl alcohol and methanol, with not more than a minor increase in the level of deleterious oxygenated by-products.

The reaction may be conducted batchwise in an autoclave using powdered catalyst or may be conducted on a continuous basis by continuously passing the contaminated MTBE feed stream or recycle stream through a continuous reactor containing a bed of a catalyst of the present invention under reaction conditions including a temperature within the range of about 120° to about 220° C., and more preferably from about 110° to about 180° C. The reaction is suitably conducted at a pressure of about 0 to about 10,000 psig, and more preferably at a pressure of about 200 to about 1,000 psig. When the reaction is conducted batchwise, contact time may suitably be from about 0.5 to 4 hours. When the reaction is conducted on a continuous basis, the methyl tertiary butyl ether feedstock should be passed through the bed of catalyst at a liquid hourly space velocity of about 0.25 to about 5 lbs. of feedstock per hour per pound of catalyst.

The reaction product, after being degassed, is suitable for use as a feed to an MTBE reactor.

The specific correlation of reaction conditions to be utilized with any specific catalyst of the present invention can be determined by one of ordinary skill in the art with comparative ease. Thus, for example, the treated methyl tertiary butyl ether feed can be analyzed after catalytic treatment to determine the level of contamination by peroxide by-products. If there is an insufficient reduction in peroxide contamination such that a significant amount (e.g., more than about 0.1 wt.%) of peroxide contaminants are still present, the severity of the reaction conditions should be increased in any suitable manner, such as by increasing one or more of the reaction temperature, the reaction pressure or the contact time. If, on the other hand, there is an undesirable increase in the level of other impurities, the reaction conditions should be ameliorated by decreasing one or more of the reaction temperature or the contact time.

The purified feed for the MTBE reactor produced by the process of the present invention will normally contain not more than about 100 ppm of tertiary butyl hydroperoxide, not more than about 100 ppm of ditertiary butyl peroxide (DTBP).

BRIEF DESCRIPTION OF THE DRAWING

The drawing is a schematic flow sheet with conventional parts omitted showing the general purification sequence that is used in accordance with the present invention in purifying methyl tertiary butyl ether.

In the drawing, for convenience, conventional parts such as heat exchangers, reflux condensers, reboilers, valves, pumps, sensor, flow control regulation apparatus, etc., have been omitted.

DESCRIPTION OF THE PREFERRED EMBODIMENT

Turning now to the drawing, there is shown a schematic flow sheet illustrating a preferred method for practicing the process of the present invention.

In accordance with a preferred embodiment of the present invention, tertiary butyl alcohol is prepared from tertiary butyl hydroperoxide by any conventional process in an appropriate tertiary butyl hydroperoxide conversion zone (not shown) in order to provide, as a reaction product, tertiary butyl alcohol contaminated with residual quantities of oxygenated by-products including ditertiary butyl peroxide, tertiary butyl hydroperoxide, other peroxides, acetone and methanol.

The contaminated tertiary butyl alcohol is reacted with methanol in a suitable reaction zone in accordance with a suitable process, such as the process shown in U.S. Pat. No. 4,822,921, U.S. Pat. No. 4,827,048, etc. to provide a methyl tertiary butyl ether reaction product contaminated with contaminants including the peroxide contaminants introduced with the contaminated tertiary butyl alcohol.

Thus, for example, the contaminated tertiary butyl alcohol may be charged by a feed line 102 to a first manifold 104. A molar excess of methanol, based on the tertiary butyl alcohol charged through the feed line 110, is also charged to the manifold 104 through a methanol feed line 112.

The mixture of contaminated tertiary butyl alcohol and methanol formed in the manifold 104 is through an intermediate feed line 106 to a second manifold 108 and thence by a charge line 110 to the reactor 100 of any suitable construction. Within the reactor 100, the tertiary butyl alcohol reacts with the methanol to form a reaction mixture comprising methyl tertiary butyl ether and contaminants including tertiary butyl hydroperoxide, ditertiary butyl peroxide and other peroxides introduced into the reactor 100 with the contaminated tertiary butyl alcohol.

The contaminated methyl tertiary butyl ether is discharged from the reactor 100 by a discharge line 114 leading to a discharge manifold 116. In accordance with the preferred embodiment of the present invention, a portion of the contaminated methyl tertiary butyl ether (e.g., 40 to 60 vol.%) is discharged from manifold 116 by a line 118 leading to a peroxide decomposition reaction zone 120 containing a bed of an acid treated clay catalyst. The peroxide decomposition zone 120 is shown in the drawing as an upflow reaction zone, but it will be understood that a downflow reaction zone can also be used, if desired.

Within the peroxide decomposition reactor, the contaminated methyl tertiary butyl ether is flowed through a bed of an acid treated clay catalyst of the present invention at a suitable flow rate, such as a rate of about 0.25 to 5 pounds of contaminated methyl tertiary butyl ether per hour per pound of acid treated clay catalyst under treating conditions including, for example, a temperature of about 100° to about 220° C., and more preferably, from about 120° to about 180° C. and a pressure of about 0 to 10,000 psig, such as a pressure of about 200 to 1,000 psig. to form a conversion product substantially free from hydroperoxide contaminants. The peroxide contaminants are converted to side products such as tertiary butyl alcohol, methanol, and isobutylene and, surprisingly additional methyl tertiary butyl ether. Thus, the conversion product 122 discharged from the peroxide decomposition zone 120 will comprise not only methyl tertiary butyl ether, but also tertiary butyl alcohol, methanol, and isobutylene.

In accordance with the present invention, the conversion product 122 is recycled to the reaction zone 100 by way of manifold 108 and feed line 110 where the tertiary butyl alcohol, methanol and isobutylene are reacted to form still more methyl tertiary butyl ether.

The other portion of the contaminated methyl tertiary butyl ether charged to the manifold 116 is discharged therefrom by a line 124 leading to a distillation zone 126 of any suitable construction where the contaminated methyl tertiary butyl ether is separated into a lighter distillation fraction 128 comprising methanol, acetone and methyl tertiary butyl ether which is charged by line 128 to the manifold 108 for recycle by line 110 to the reaction zone 100.

Purified methyl tertiary butyl ether substantially free from peroxide contaminants such as tertiary butyl hydroperoxide and ditertiary butyl peroxide is discharged from the distillation zone 126 as a heavier distillation fraction 130.

The invention is further illustrated by the following working examples, which are given by way of illustration and not as limitations on the scope of the present invention.

WORKING EXAMPLES

Reactor

The reactor was a stainless steel tube (0.51×29″) which was electrically heated. The catalyst bed (if any) was 100 cc. Liquid feed was pumped into the bottom of the reactor. Pressure regulation was with a Skinner Uni-Flow valve and a Foxboro controller. The liquid feed was pumped with a Ruska dual drive pump.

Feed

The typical recycle feed for the decomposition reactor was 10% water, 51% methanol, 35.5% TBA, 1.0% MTBE, and 2.5% DTBP.

Details for the runs are given in the attached tables.

TABLE 1

| REMOVAL OF PEROXIDES FROM AN MTBE RECYCLE STREAM | | | | | |
|---|---|---|---|---|---|
| Notebook Number | 6773-16-M | 6773-41-1 | 6773-41-2 | 6773-41-3 | 6773-41-4 |
| Catalyst | | Clay-24 | Clay-24 | Clay-24 | Clay-24 |
| Reactor (cc) | | 100 | 100 | 100 | 100 |
| Pressure (psig) | | 500 | 500 | 500 | 500 |
| Feed Rate (cc/hr) | | 100 | 100 | 100 | 100 |
| Temperature (°C.) | | 120 | 140 | 160 | 180 |
| Time on Stream (hr) | | 4 | 4 | 4 | 4 |
| Space Vel. (cc/cc) | | 1.0 | 1.0 | 1.0 | 1.0 |
| DTBP Conv. (%) | | 5.8 | 64.6 | 99.8 | 100.0 |
| TBA Conversion (%) | | 66.9 | 67.5 | 70.9 | 75.7 |
| Remarks | H2O Free Basis | H2O Free Basis | H2O Free Basis | H2O Free Basis | H2O Free Basis |
| Isobutylene | 0.003 | 0.829 | 0.988 | 2.033 | 2.600 |
| MEOH | 54.786 | 51.205 | 52.630 | 53.449 | 66.751 |
| Acetone | 0.009 | 0.110 | 0.623 | 1.256 | 1.925 |
| MTBE | 1.225 | 31.162 | 29.794 | 25.356 | 13.616 |
| TBA | 40.795 | 13.490 | 13.252 | 11.882 | 9.927 |
| DTBP | 2.789 | 2.626 | 0.988 | 0.006 | 0.000 |

TABLE 2
REMOVAL OF PEROXIDES FROM AN MTBE RECYCLE STREAM

| Notebook Number | 6773-16-M | 6773-42-1 | 6773-42-2 | 6773-42-3 | 6773-42-4 |
|---|---|---|---|---|---|
| Catalyst |  | Clay-24 | Clay-24 | Clay-24 | Clay-24 |
| Reactor (cc) |  | 100 | 100 | 100 | 100 |
| Pressure (psig) |  | 500 | 500 | 500 | 500 |
| Feed Rate (cc/hr) |  | 200 | 200 | 200 | 200 |
| Temperature (°C.) |  | 120 | 140 | 160 | 180 |
| Time on Stream (hr) |  | 4 | 4 | 4 | 4 |
| Space Vel. (cc/cc) |  | 2.0 | 2.0 | 2.0 | 2.0 |
| DTBP Conv. (%) |  | 1.4 | 38.9 | 97.2 | 100.0 |
| TBA Conversion (%) |  | 67.1 | 69.4 | 72.2 | 76.6 |
| Remarks | H2O Free Basis | H2O Free Basis | H2O Free Basis | H2O Free Basis | H2O Free Basis |
| Isobutylene | 0.003 | 0.867 | 3.242 | 4.189 | 4.338 |
| MEOH | 54.786 | 51.474 | 50.796 | 52.459 | 57.490 |
| Acetone | 0.009 | 0.067 | 0.399 | 1.151 | 1.616 |
| MTBE | 1.225 | 30.986 | 30.020 | 26.653 | 18.952 |
| TBA | 40.795 | 13.413 | 12.500 | 11.345 | 9.557 |
| DTBP | 2.789 | 2.750 | 1.703 | 0.079 | 0.000 |

TABLE 3
REMOVAL OF PEROXIDES FROM AN MTBE RECYCLE STREAM

| Notebook Number | 6773-16-M | 6773-43-1 | 6773-43-2 | 6773-43-3 | 6773-43-4 |
|---|---|---|---|---|---|
| Catalyst |  | Clay-24 | Clay-24 | Clay-24 | Clay-24 |
| Reactor (cc) |  | 100 | 100 | 100 | 100 |
| Pressure (psig) |  | 500 | 500 | 500 | 500 |
| Feed Rate (cc/hr) |  | 400 | 400 | 400 | 400 |
| Temperature (°C.) |  | 120 | 140 | 160 | 180 |
| Time on Stream (hr) |  | 4 | 4 | 4 | 4 |
| Space Vel. (cc/cc) |  | 4.0 | 4.0 | 4.0 | 4.0 |
| DTBP Conv. (%) |  | 0.0 | 9.4 | 61.5 | 99.5 |
| TBA Conversion (%) |  | 64.5 | 69.8 | 70.8 | 74.4 |
| Remarks | H2O Free Basis | H2O Free Basis | H2O Free Basis | H2O Free Basis | H2O Free Basis |
| Isobutylene | 0.003 | 2.306 | 3.259 | 3.248 | 3.477 |
| MEOH | 54.786 | 50.426 | 50.505 | 53.655 | 57.601 |
| Acetone | 0.009 | 0.038 | 0.135 | 0.678 | 1.443 |
| MTBE | 1.225 | 29.565 | 30.491 | 27.213 | 22.203 |
| TBA | 40.795 | 14.463 | 12.312 | 11.926 | 10.462 |
| DTBP | 2.789 | 2.870 | 2.527 | 1.074 | 0.014 |

TABLE 4
REMOVAL OF PEROXIDES FROM AN MTBE RECYCLE STREAM

| Notebook Number | 6773-16-Q | 6773-64-1 | 6773-64-2 | 6773-64-3 | 6773-64-4 |
|---|---|---|---|---|---|
| Catalyst |  | Glass Beads | Glass Beads | Glass Beads | Glass Beads |
| Reactor (cc) |  | 100 | 100 | 100 | 100 |
| Pressure (psig) |  | 500 | 500 | 500 | 500 |
| Feed Rate (cc/hr) |  | 400 | 400 | 400 | 400 |
| Temperature (°C.) |  | 150 | 160 | 170 | 180 |
| Time on Stream (hr) |  | 4 | 4 | 4 | 4 |
| Space Vel. (cc/cc) |  | 4.0 | 4.0 | 4.0 | 4.0 |
| DTBP Conv. (%) |  | 15.9 | 41.6 | 62.7 | 81.0 |
| TBA Conversion (%) |  | 0.0 | 0.0 | 0.0 | 0.0 |
| Remarks | H2O Free Basis | H2O Free Basis | H2O Free Basis | H2O Free Basis | H2O Free Basis |
| Isobutylene | 0.004 | 0.002 | 0.003 | 0.003 | 0.003 |
| MEOH | 55.631 | 55.700 | 55.539 | 55.413 | 55.384 |
| Acetone | 0.000 | 0.164 | 0.528 | 0.838 | 1.115 |
| MTBE | 1.213 | 1.236 | 1.194 | 1.195 | 1.207 |
| TBA | 40.024 | 40.198 | 40.739 | 41.076 | 41.245 |
| DTBP | 2.765 | 2.324 | 1.615 | 1.030 | 0.525 |

Significant and unexpected differences are noted when comparing the runs for uncatalyzed (glass beads) decomposition of ditertiary butyl peroxide (DTBP) with those for the catalyzed (Clay-24) decomposition. In runs conducted in the absence of a catalyst under reaction conditions including a temperature of 160° C. and a space velocity of 4.0, 41.6% of the DTBP was decomposed (6773-64-2). Under the same conditions with Clay 24 catalyst, 99.8% of the DTBP was decomposed. Thus, at this temperature, the peroxide decomposes more than twice as fast in the presence of a catalyst. In addition, the clay catalyst is an excellent catalyst for the production of methyl tertiary butyl ether.

Also, when the runs for the uncatalyzed and catalyzed decomposition with similar DTBP conversions are compared, there is a difference in the percentage of acetone formed. An uncatalyzed run at 170° C. (6773-64-3) shows 62.7% of DTBP conversion and the formation of 1.195% of acetone. A catalyzed run with Clay 24 (8773-41-2) at 140° C. shows a 64.6% DTBP conversion but only 0.623% of acetone was formed.

The foregoing examples are given by way of illustration only, and are not intended as limitations on the scope of this invention, as defined by the appended claims.

Having thus described our invention, what is claimed is:

1. A method for removing the peroxides from a methyl tertiary butyl ether feedstock contaminated with residual quantities of peroxides including ditertiary butyl peroxide, which comprises the steps of:

contacting said feedstock in a reaction zone with an acid treated clay catalyst at a temperature of about 120° to about 220° C. for a period of time sufficient to substantially selectively decompose said peroxides, including said ditertiary butyl peroxide.

2. A method as in claim 1 wherein reaction is conducted at a temperature of about 120° to about 180° C.

3. A method as in claim 1 wherein the acid-treated clay catalyst is an acid-treated smectite type of clay.

4. A method as in claim 3 wherein the smectite type of clay is a montmorillonite type of clay treated with a mineral acid.

5. A method as in claim 4 wherein the mineral acid is selected from the group including sulfuric acid, phosphoric acid and hydrochloric acid.

6. A method for removing peroxides from a methyl tertiary butyl ether recycle stream contamined with residual quantities of peroxides, including ditertiary butyl peroxide, comprising the steps of:

contacting said feedstock in a reaction zone with an acid treated montmorillonite clay catalyst at a temperature of about 120° to about 180° C. at a pressure of about 200 to 1,000 psig. for a period of time sufficient to substantially selectively decompose said peroxides, including said ditertiary butyl peroxide to side products including tertiary butyl alcohol, methanol and acetone, to thereby provide a reactor effluent from said reaction containing not more than about 100 ppm of tertiary butyl hydroperoxide and not more than about 100 ppm of ditertiary butyl peroxide.

* * * * *